(12) United States Patent
Wells et al.

(10) Patent No.: US 6,177,669 B1
(45) Date of Patent: Jan. 23, 2001

(54) VORTEX GAS FLOW INTERFACE FOR ELECTROSPRAY MASS SPECTROMETRY

(75) Inventors: Gregory J. Wells, Fairfield; Roger C. Tong, Berkeley; Peter P. Yee, San Ramon, all of CA (US)

(73) Assignee: Varian, Inc., Pslo Alto, CA (US)

( * ) Notice: Under 35 U.S.C. 154(b), the term of this patent shall be extended for 0 days.

(21) Appl. No.: 09/162,258

(22) Filed: Sep. 28, 1998

(51) Int. Cl.⁷ .............................. B01D 59/44; H01J 49/00
(52) U.S. Cl. ....................... 250/288; 250/492.1
(58) Field of Search ............................................. 250/288

(56) References Cited

U.S. PATENT DOCUMENTS

| 4,531,056 | 7/1985 | Labowsky et al. . | |
| 4,861,988 | 8/1989 | Henion et al. . | |
| 4,885,076 | 12/1989 | Smith et al. | 204/299 |
| 5,157,260 | 10/1992 | Mylchreest et al. | 250/423 |
| 5,412,208 | * 5/1995 | Covey et al. | 250/288 |
| 5,581,081 | * 12/1996 | Kato et al. | 250/288 |

FOREIGN PATENT DOCUMENTS

715337A1  * 6/1996 (EP) .
0 715 337 A1   6/1996 (EP) .

* cited by examiner

Primary Examiner—Teresa M. Arroyo
Assistant Examiner—Johnnie L. Smith, II
(74) Attorney, Agent, or Firm—Edward H. Berkowitz (57) ABSTRACT

An apparatus for efficiently removing a carrier liquid from charged liquid drops formed by electrospray ionization prior to introduction of the drops into a mass spectrometer. A central capillary tube connects a region of the low pressure vacuum system containing the mass spectrometer with a region at substantially atmospheric pressure, in which ion formation is produced by electrospray ionization. Heated, drying gas flows through a plurality of vortex forming channels symmetrically disposed about the axis of the central capillary tube which provides an entrance to the spectrometer. Gas exiting the vortex forming channels enters tangentially to the inside of a vortex drying tube with a small helix angle, causing the gas to swirl around the tube, forming a vortex. The vortex drying gas flows in a direction that is substantially transverse to the axis of the entrance capillary into the mass spectrometer. The vortex gas intersects the electrospray, separating undesired large drops from smaller drops by a vortex gas flow which imparts a centrifugal force to the drops. The largest drops are driven to the wall of the drying tube and caused to fragment into smaller drops by evaporation and collision with the wall.

12 Claims, 12 Drawing Sheets

VORTEX GAS FLOW INTERFACE FOR ELECTROSPRAY MASS SPECTROMETRY

FIELD OF THE INVENTION

The present invention relates to apparatus and methods for characterizing materials using mass spectrometry, and more specifically, to an apparatus which reduces the measurement noise which results from the formation of large charged drops during use of the electrospray technique.

BACKGROUND OF THE INVENTION

Mass spectrometers have become common tools in chemical analysis. Generally, mass spectrometers operate by separating ionized atoms or molecules based on differences in their mass-to-charge ratio (m/e). A variety of mass spectrometer devices are commonly in use, including ion traps, quadrupole mass filters, and magnetic sector mass analyzers.

The general stages in performing a mass-spectrometric analysis are: (1) create gas-phase ions from a sample; (2) separate the ions in space or time based on their mass-to-charge ratio; and (3) measure the quantity of ions of each selected mass-to-charge ratio. Thus, in general, a mass spectrometer system consists of an ion source, a mass-selective analyzer, and an ion detector. In the mass-selective analyzer, magnetic and electric fields may be used, either separately or in combination, to separate the ions based on their mass-to-charge ratio. Hereinafter, the mass-selective analyzer portion of a mass spectrometer system will simply be called a mass spectrometer. Ions introduced into a mass spectrometer are separated in a vacuum environment. Accordingly, it is necessary to prepare the sample undergoing analysis for introduction into this environment. This presents particular problems for high molecular weight compounds or other sample materials which are difficult to volatilize. While liquid chromatography is well suited to separate a liquid sample matrix into its constituent components, it is difficult to introduce the output of a liquid chromatograph (LC) into the vacuum environment of a mass spectrometer. One technique that has been used for this purpose is the electrospray method.

The "electrospray" or "electrospray ionization" technique is used to produce gas-phase ions from a liquid sample matrix to permit introduction of the sample into a mass spectrometer. It is thus useful for providing an interface between a liquid chromatograph and a mass spectrometer. In the electrospray method, the liquid sample to be analyzed is pumped through a capillary tube or needle. A high electrical potential (typically, 3 to 4 thousand volts) is established between the end of the needle and an opposing wall or other structure. The stream of liquid issuing from the needle tip is broken up into highly charged drops by the electric field, forming the electrospray. An inert gas, such as dry nitrogen (for example), may also be introduced through a surrounding capillary to enhance nebulization (droplet formation) of the fluid stream.

The electrospray drops consist of sample compounds in a carrier liquid and are electrically charged by the electric potential as they exit the capillary needle. The charged drops are transported in an electric field and injected into the mass spectrometer, which is maintained at a high vacuum. Through the combined effects of a drying gas and vacuum, the carrier liquid in the drops starts to evaporate giving rise to smaller, increasingly unstable drops from which surface ions are liberated into the vacuum for analysis. The desolvated ions pass through a sample aperture and ion lenses, and are focused into the high vacuum region of the mass spectrometer, where they are separated according to mass-to-charge ratio and detected by an appropriate detector (e.g., a photo-multiplier tube). In addition to, or in place of an electrostatic ion lens, a multipole RF ion guide may be used to transport the ions to the mass spectrometer.

Although the electrospray method is very useful for analyzing high molecular weight dissolved samples, it does have some limitations. For example, commercially available electrospray devices are limited to liquid flow rates of less than 20–30 microliters/min. Higher liquid flow rates result in unstable and inefficient ionization of the dissolved sample. Since the electrospray needle is typically connected to a liquid chromatograph, this acts as a limitation on the flow from the chromatograph.

One method of improving the performance of electrospray devices at higher liquid flow rates is to utilize a pneumatically assisted electrospray needle. One example of such a needle is formed from two concentric, capillary tubes. In such a device the sample containing liquid flows through the inner tube and a nebulizing gas flows through the annular space between the two tubes. This improves the efficiency of the ionization process by improving the ability of the electrospray needle to form drops from the sample liquid. However, at high sample liquid flow rates into this type of electrospray needle, the drops formed are relatively large and can degrade the performance of the mass spectrometer (by increasing the noise) if allowed to enter the device. This makes such electrospray needles difficult to use with liquid chromatographs.

As noted, large charged drops entering a mass spectrometer degrade its performance, and it is therefore desirable to eliminate or reduce the size of these drops. One mechanism to accomplish this is to employ electrostatic dispersion of drops, which occurs when coulomb forces exceed those due to surface tension. It is known that the surface tension is reduced by reducing the drop size through evaporation. As the drop size is reduced, the relative effect of the coulomb forces increases, causing the drops to spontaneously break up into smaller drops. Evaporation of the carrier liquid(s) from the drops permits the effect of the coulomb force to dominate that of the surface tension, with the benefit of decreasing the system noise of the mass spectrometer.

Thus, one way of reducing the noise problem caused by the larger drops produced by an electrospray needle is to employ means to reduce droplet size prior to injection into the mass spectrometer. One method of accomplishing this is shown in the prior art electrospray mass spectrometer interface 100 of FIG. 1. As shown in the figure, a liquid sample matrix flows through electrospray needle 102 and out of the needle's outlet, causing the liquid to form drops which are directed towards entrance orifice 104 of a mass spectrometer. A laminar flow of heated inert gas 106 is formed in a direction substantially counter to that of the flow from the outlet of needle 102, with the heated drying gas placed between the outlet of the electrospray needle and capillary tube 108 which serves as the entrance to the mass spectrometer 109. The heated inert gas facilitates evaporation of the solvent from the liquid drops, reducing their size, and acts to displace vapor formed from the evaporation process away from the entrance to the mass spectrometer. This is intended to reduce excess noise in the measurements made by the mass spectrometer.

Figure 2:
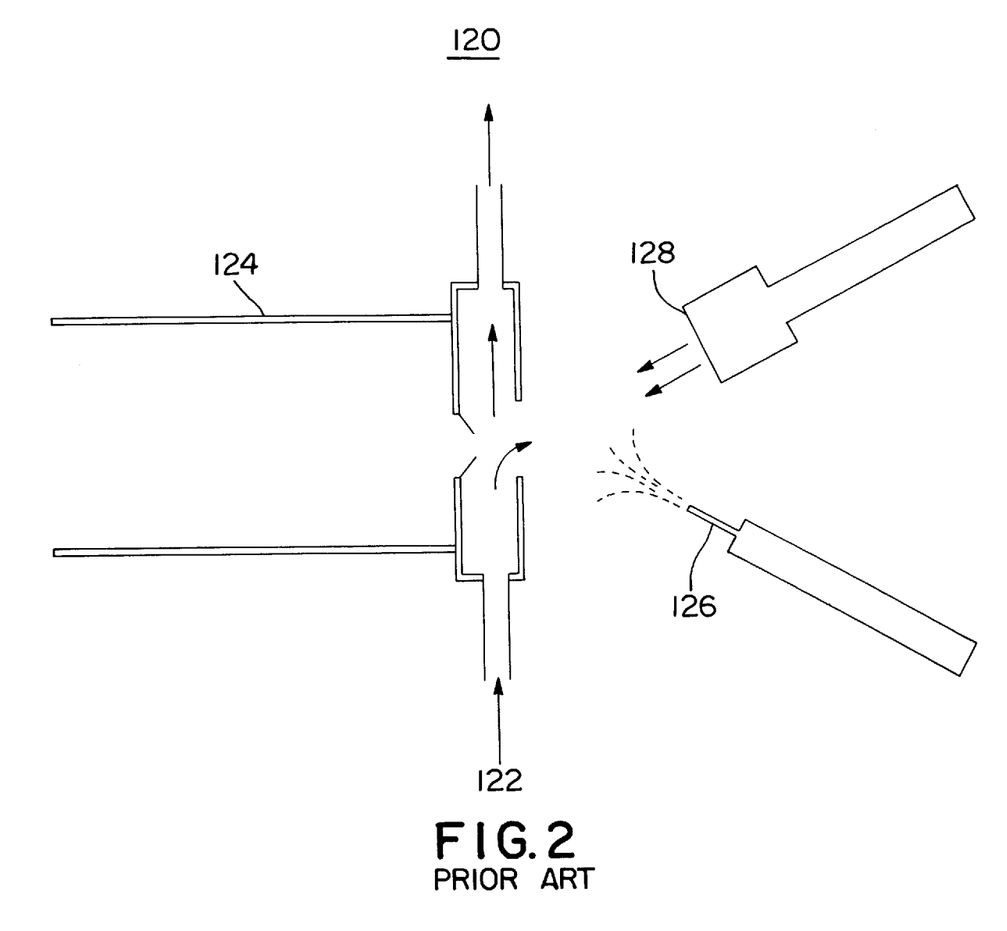

In another prior art electrospray mass spectrometer interface 120 shown in FIG. 2, a drying gas 122 is arranged to flow in a transverse direction relative to entrance orifice 124 of the mass spectrometer. In addition, the direction of the 
sprayed drops produced by electrospray needle 126 is oriented at an angle off of the axis of the orifice. A second flow of heated drying gas 128, in a direction different from that of drying gas 122, intersects the droplet flow from needle 126 in a region upstream of the orifice (i.e., to the right of the orifice in the figure). Gas flows 122 and 128 mix, with the second flow 128 helping to evaporate the drops to produce ions and move the evaporating drops and ions toward the spectrometer orifice.

Figure 1:
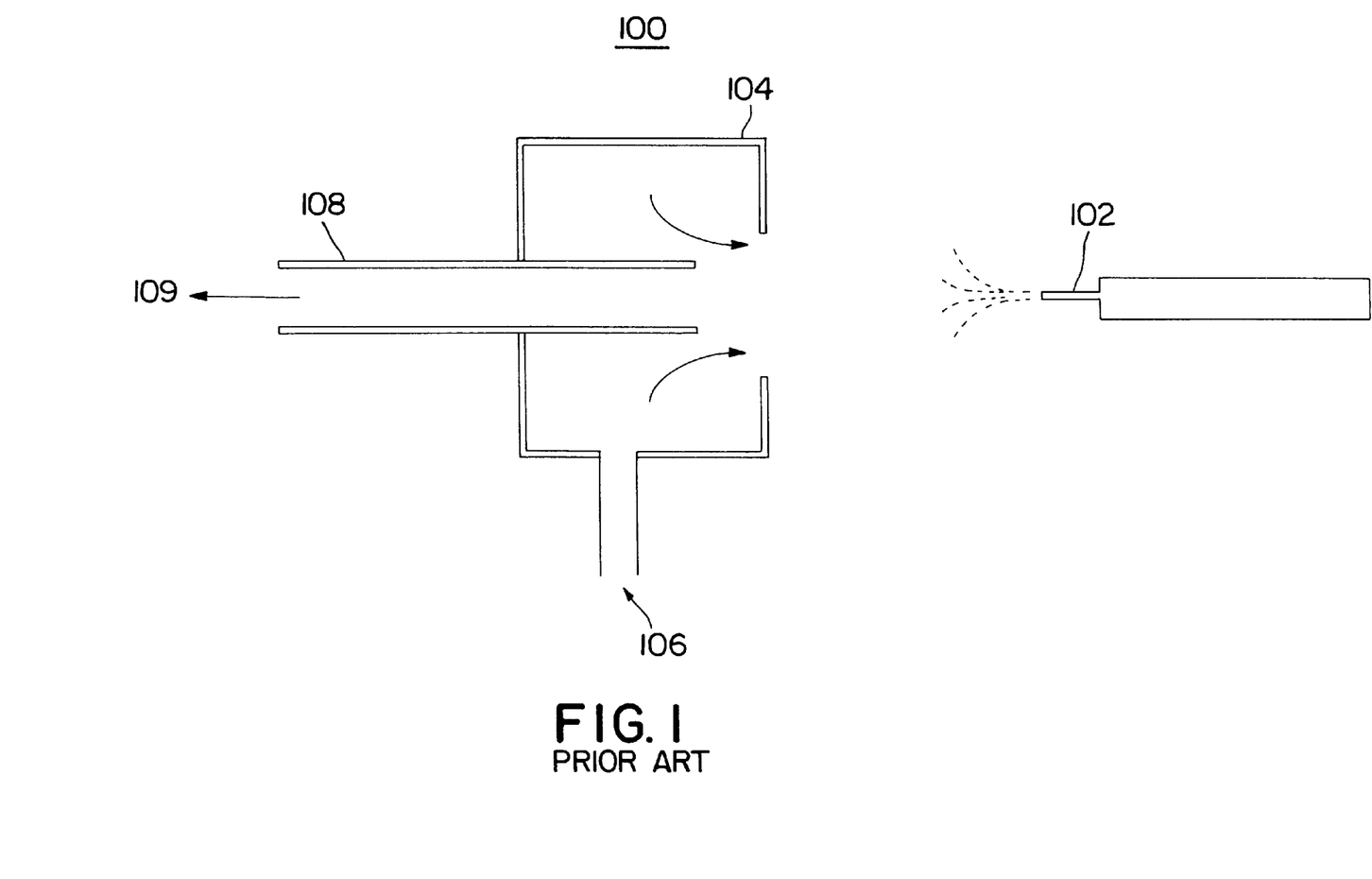

The prior art devices shown in FIGS. 1 and 2 have the disadvantage of requiring a relatively large volume of drying gas flowing counter to the direction of movement of the electrospray drops (or at some angle with respect to the direction of motion of the drops). The drying gas removes the carrier liquid(s) from the smaller charged drops, but does not efficiently separate the larger drops from smaller ones. Large drops will not be completely desolvated by the time they reach the sampling aperture into the mass spectrometer, unless very large drying gas flows are used. However, such larger gas flow rates can impede transfer of the ions into the orifice of the mass spectrometer.

Another disadvantage of the prior art devices is the formation of salt deposits at the capillary inlet to the spectrometer when nonvolatile salts are present in the sample liquid matrix. This is a problem when using high liquid flow rates into the electrospray needle in combination with high nebulizing gas flows, as in the previously described prior art device formed from concentric tubes. The problem arises because large drops that reach the entrance orifice into the mass spectrometer carry with them dissolved nonvolatile salts.

What is desired is an apparatus which provides an improved method of removing carrier liquid(s) from charged liquid drops formed by electrospray ionization. It is further desired to provide a method to improve the transfer of charged sample ions formed by electrospray ionization into a mass spectrometer. It is also desired to provide a method of removing large, charged drops that form when high liquid flow rates are used with electrospray ionization, prior to the large drops entering the mass spectrometer.

SUMMARY OF THE INVENTION

The present invention is directed to an electrospray apparatus for efficiently removing carrier liquid(s) from charged drops formed by electrospray ionization prior to introduction of the drops to a mass spectrometer. A central capillary tube (or other structure such as a skimmer cone or orifice) connects a region of the low pressure vacuum system containing the mass spectrometer with a region at substantially atmospheric pressure, in which ions are produced by electrospray ionization. Heated, drying gas flows through one or more vortex forming channels symmetrically disposed about the axis of the central capillary tube which serves as an entrance to the spectrometer, where the central capillary tube extends through the center of the vortex forming insert. Heating elements heat the end of the central capillary and the drying gas as it enters the vortex forming channels. Gas exiting the vortex forming channels enters tangentially to the inside of a vortex drying tube with a small helix angle, causing the gas to swirl around the tube, forming a vortex.

The vortex drying gas flows in a direction that is substantially transverse to the axis of the entrance capillary to the mass spectrometer. When the vortex gas flow reaches the electrospray, it separates undesired large drops from smaller drops by centrifugal force. The largest drops are driven to the wall of the drying tube by the centrifugal force and fragmented into smaller drops by evaporation and collision with the wall. This prevents the larger drops from entering the mass spectrometer and producing excess noise in the measurements.

BRIEF DESCRIPTION OF THE DRAWINGS

FIG. 1 is a schematic diagram showing a first prior art apparatus for reducing the number and size of large charged drops which enter a mass spectrometer after production by an electrospray needle.

FIG. 2 is a schematic diagram showing a second prior art apparatus for reducing the number and size of large charged drops which enter a mass spectrometer after production by an electrospray needle.

FIG. 3 is a schematic diagram showing a first embodiment of the vortex gas flow interface for electrospray mass spectrometry of the present invention.

FIG. 4 is a graph showing the signal from an electrometer representing the ion current measured at the exit of the central capillary tube inside of the vacuum chamber for the prior art electrospray device shown in FIG. 1.

FIG. 5 is a graph showing the signal from the electrometer for the vortex gas flow interface of the present invention shown in FIG. 3, under the same drying gas flow and temperature conditions as those used to obtain the data for FIG. 4.

FIG. 6 is a schematic diagram showing an alternative arrangement of the vortex gas flow interface of FIG. 3 and an electrospray needle.

FIG. 7 is a schematic diagram showing another alternative arrangement of the vortex gas flow interface of FIG. 3 and an electrospray needle.

FIG. 8 is a schematic diagram showing still another arrangement of the vortex gas flow interface of FIG. 3 and an electrospray needle.

FIG. 9 is a schematic diagram showing a different embodiment of the vortex gas flow interface for electrospray mass spectrometry of the present invention.

FIG. 10 is a schematic diagram showing yet another embodiment of the vortex gas flow interface for electrospray mass spectrometry of the present invention.

FIG. 11 is a schematic diagram showing an embodiment of the present invention which incorporates a sampling orifice and skimmer cone.

FIG. 12 is a schematic diagram showing an embodiment of the apparatus of FIG. 11 which incorporates a conical sampling orifice.

DETAILED DESCRIPTION OF THE INVENTION

The present invention is directed to an apparatus for facilitating the use of a liquid chromatograph (LC) with a vacuum instrument such as a mass spectrometer (MS), and is described in connection with an interface placed between the input port of a mass spectrometer and the output of an electrospray needle used to form charged drops of a liquid sample matrix. The interface of the present invention forms a vortex gas flow which intersects the flow of charged drops from the electrospray needle, with the vortex flow direction oriented substantially transverse to the droplet flow direction. The vortex gas flow separates the larger drops from the smaller ones by imparting a centrifugal force to the drops. The present invention provides several advantages over prior art methods of reducing the number of large drops injected by electrospray into a mass spectrometer, including: (1) improved separation of undesired large drops from smaller drops; (2) improved removal of carrier liquid(s) from charged drops, thereby preventing the formation of salt deposits at the capillary entrance to the mass spectrometer; (3) improved transport of charged sample ions into the mass spectrometer by enhancing the pressure gradient between the entrance to the spectrometer and the surrounding region where the electrosprayed drops reside; and (4) improved transport of charged sample ions into the mass spectrometer by providing an insulating vortex drying tube which confines the charged drops in the radial direction as they move towards the entrance to the spectrometer.

Figure 3:
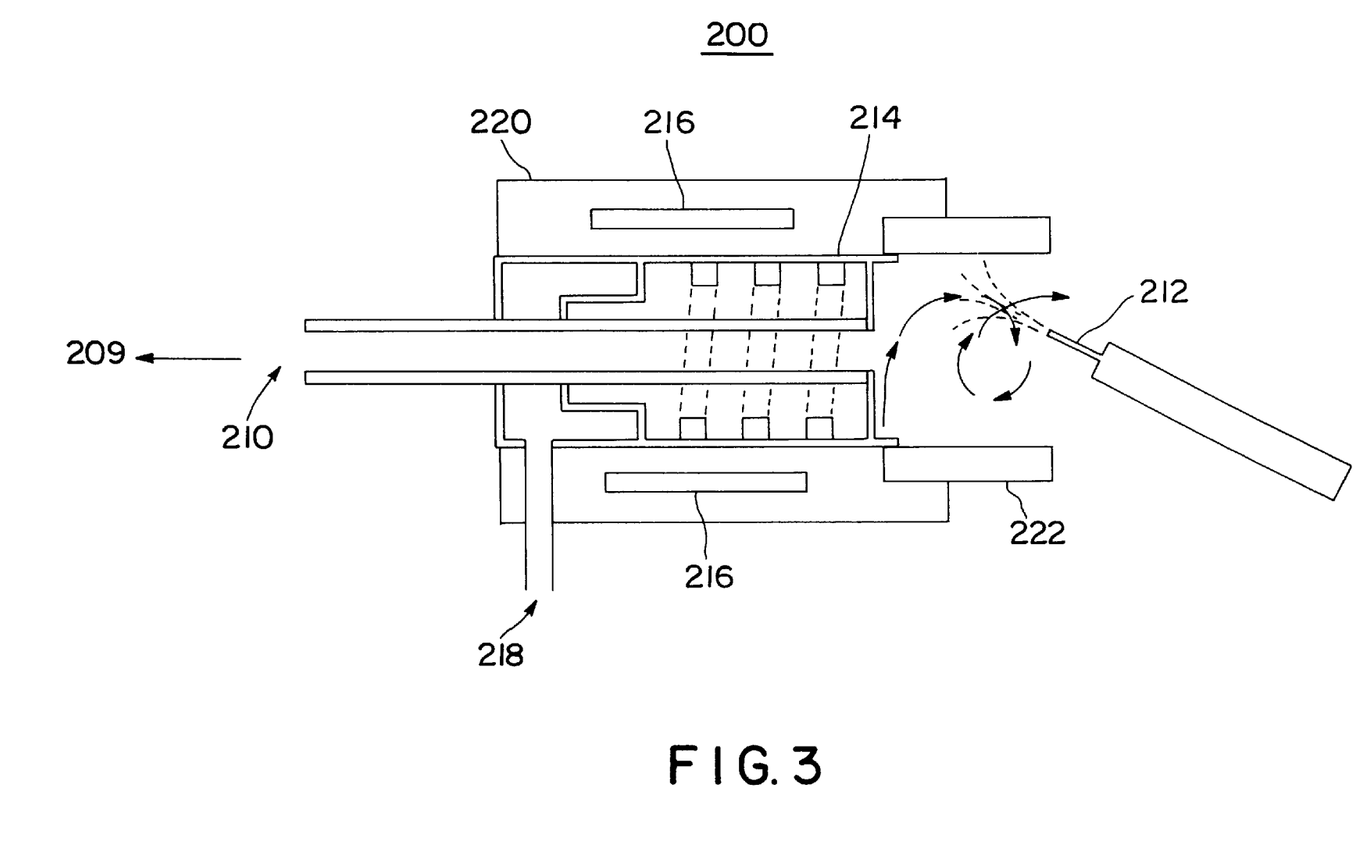

FIG. 3 is a schematic diagram showing a first embodiment of the present invention, showing the vortex gas flow interface 200 for electrospray injection into a mass spectrometer. A central capillary tube 210 (or in the alternative an orifice or skimmer cone) connects a region held at low pressure by a vacuum system and containing the mass spectrometer 209, with a region at substantially atmospheric pressure in which ions are produced by electrospray needle 212. A drying gas flows through a plurality of vortex forming channels 214 disposed about the longitudinal axis of central capillary tube 210. Preferably, the drying gas is heated for improved drying efficiency. The gas 218 may be heated by heating element 216 in the flow path of drying gas 218.

Vortex forming gas channels 214 can be made by machining interleaved multi-start threads or channels into a metal insert, and press fitting the insert into a metal retaining structure (such as element 220 of the figure). The channels may be of any selected cross-section. In this embodiment, central capillary tube 210 extends through the center of the vortex forming insert. As noted, heating elements 216 in retaining structure 220 act to heat the end of central capillary 210 and drying gas 218 as it enters the vortex forming structure. Gas exiting vortex forming channels 214 enters tangentially to the inside of vortex drying tube 222 and with a small helix angle, causing the gas to swirl around the tube, forming a vortex gas flow. The channels form helical threads which extend the entire length of the insert. Each channel has an inlet and an outlet.

The swirling flow of the drying gas encounters the electrospray ejected from needle 212 in vortex drying tube 222. The vortex gas flow acts to separate undesired large drops from smaller drops in the electrospray by imparting a rotational motion, and hence centrifugal force to the drops. This causes the largest drops to be driven into the wall of drying tube 222 where some of them are fragmented into smaller drops by a combination of evaporation and collision with the wall. The region of the vortex flow closer to central capillary 210 is at a pressure that is substantially below the pressure near the walls of drying tube 222. This is primarily the result of two effects: (1) the radial pressure gradient formed by the vortex; and (2) the vacuum from the central capillary tube.

An electrospray needle 212 with a gas nebulizer may be used to create the charged drops that are sprayed into vortex gas flow interface 200. The gas nebulizer can be of the multi-capillary tube type disclosed in the U.S. patent application Ser. No. 09/162,261 entitled, "Pneumatically Assisted Electrospray Device with Alternating Pressure Gradients for Mass Spectrometry," assigned to the same assignee and filed the same day as the present application, the contents of which are hereby incorporated by reference.

In the preferred embodiment of the present invention, the output of electrospray needle 212 is directed at an angle with respect to the axis of capillary tube 210, with its output end directed towards the wall of vortex drying tube 222 where the vortex gas has its greatest velocity. Although a variety of materials may be used, it is desirable to form vortex drying tube 222 from quartz or another electrical insulator. It is believed that charging of the insulating surface of vortex drying tube 222 by the drops which collide with it is beneficial for two reasons: (1) it assists in containing the drops in the radial direction by providing a repulsive coulomb force on the drops entering the entrance capillary; and (2) it aids in the fission of the drops into smaller drops by increasing the disruptive coulomb forces on the drops.

Figure 4:
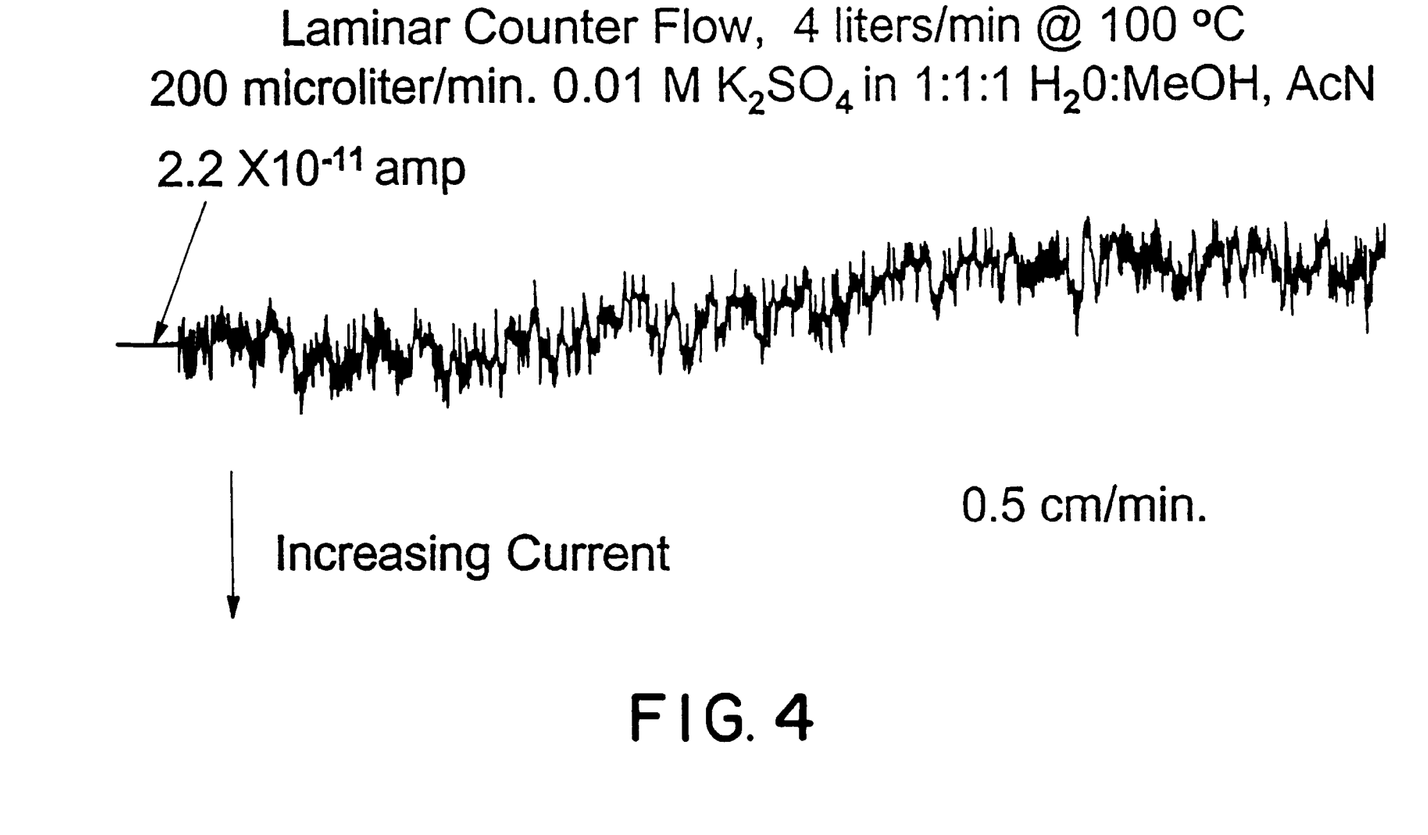
Figure 5:
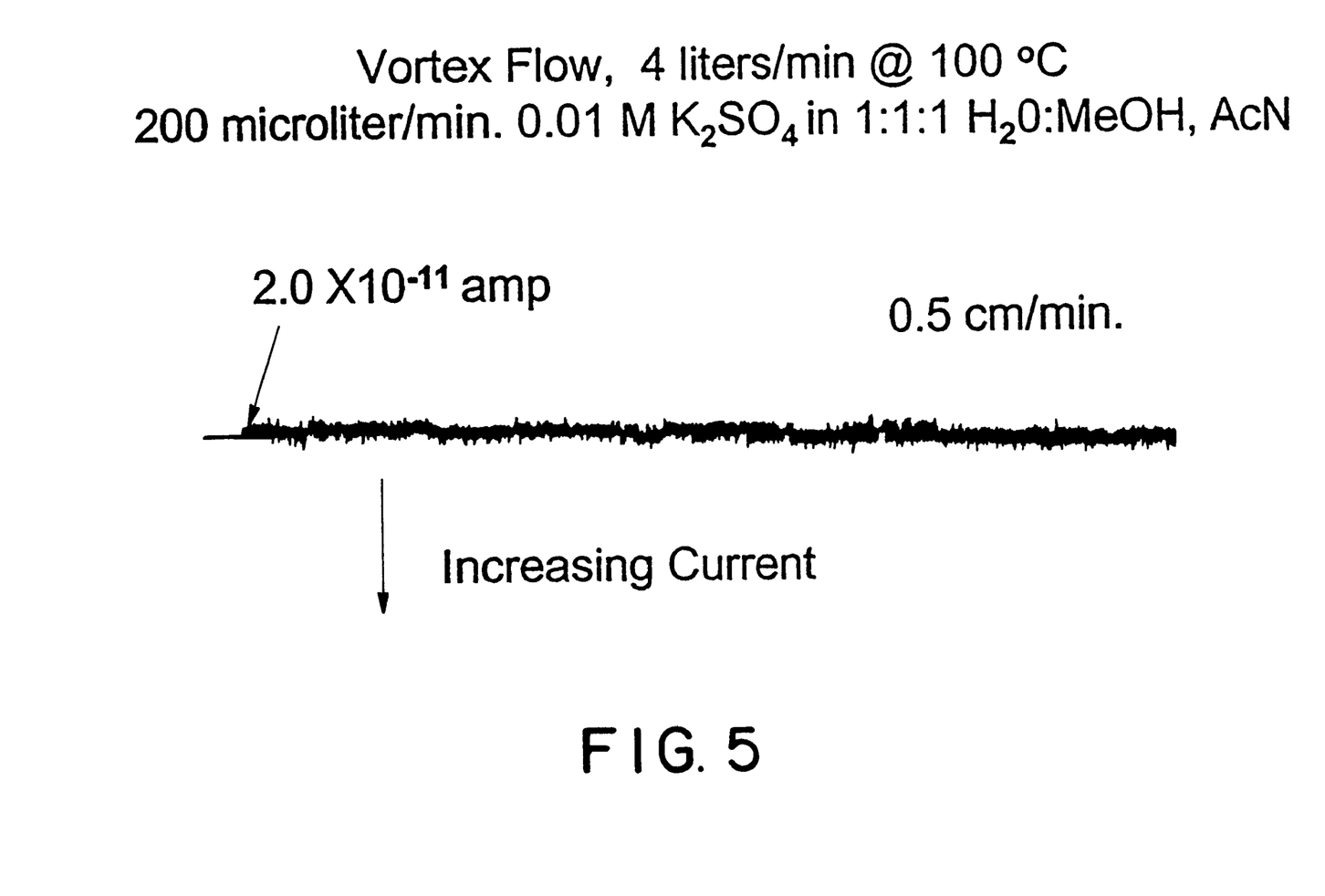

FIG. 4 shows the output signal from an electrometer (with 0.2 millisecond time constant) of the ion current measured at the exit of the central capillary tube inside of the vacuum chamber for the prior art electrospray device shown in FIG. 1. The data shown in FIG. 4 was obtained using a laminar counter flow of nitrogen of 4 liters/minute and a gas temperature of 100° C. FIG. 5 shows the signal from the electrometer for the vortex gas flow interface of the present invention shown in FIG. 3 under the same drying gas flow and temperature conditions as those used to obtain the data for FIG. 4. The reduction in the peak-to-peak noise that is observed in FIG. 5 as compared to FIG. 4, along with only a small reduction in the average ion current, is an indication of the reduced droplet size achieved using the inventive vortex flow interface.

Figure 6:
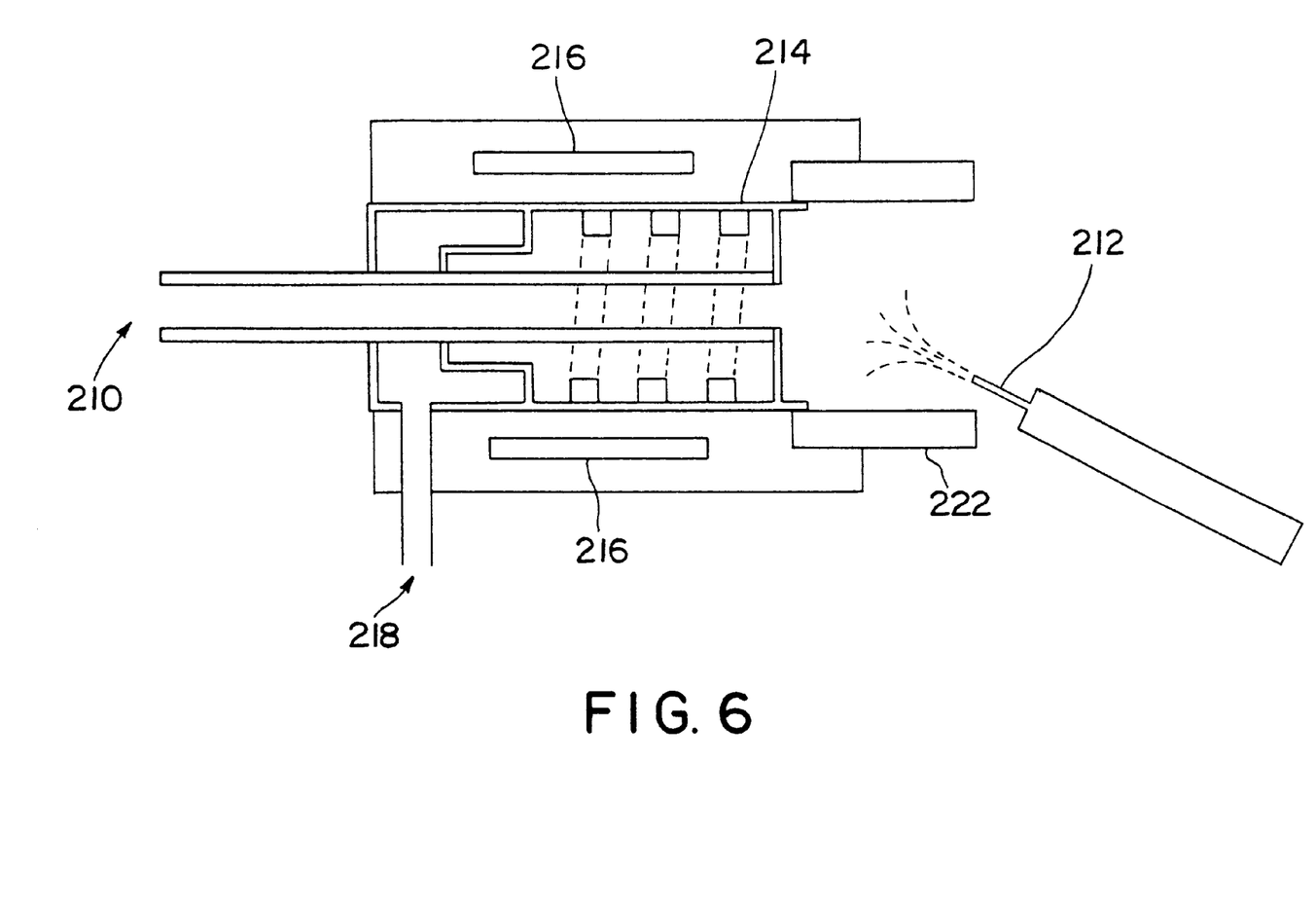

FIG. 6 is a schematic diagram showing an alternative arrangement of the vortex gas flow interface of FIG. 3 and an electrospray needle. In the embodiment of FIG. 6, the axis of electrospray needle 212 is directed more towards the entrance of central capillary 210 instead of the wall of drying tube 222, as for the embodiment of FIG. 3, but is still at an angle relative to the axis of tube 210.

Figure 7:
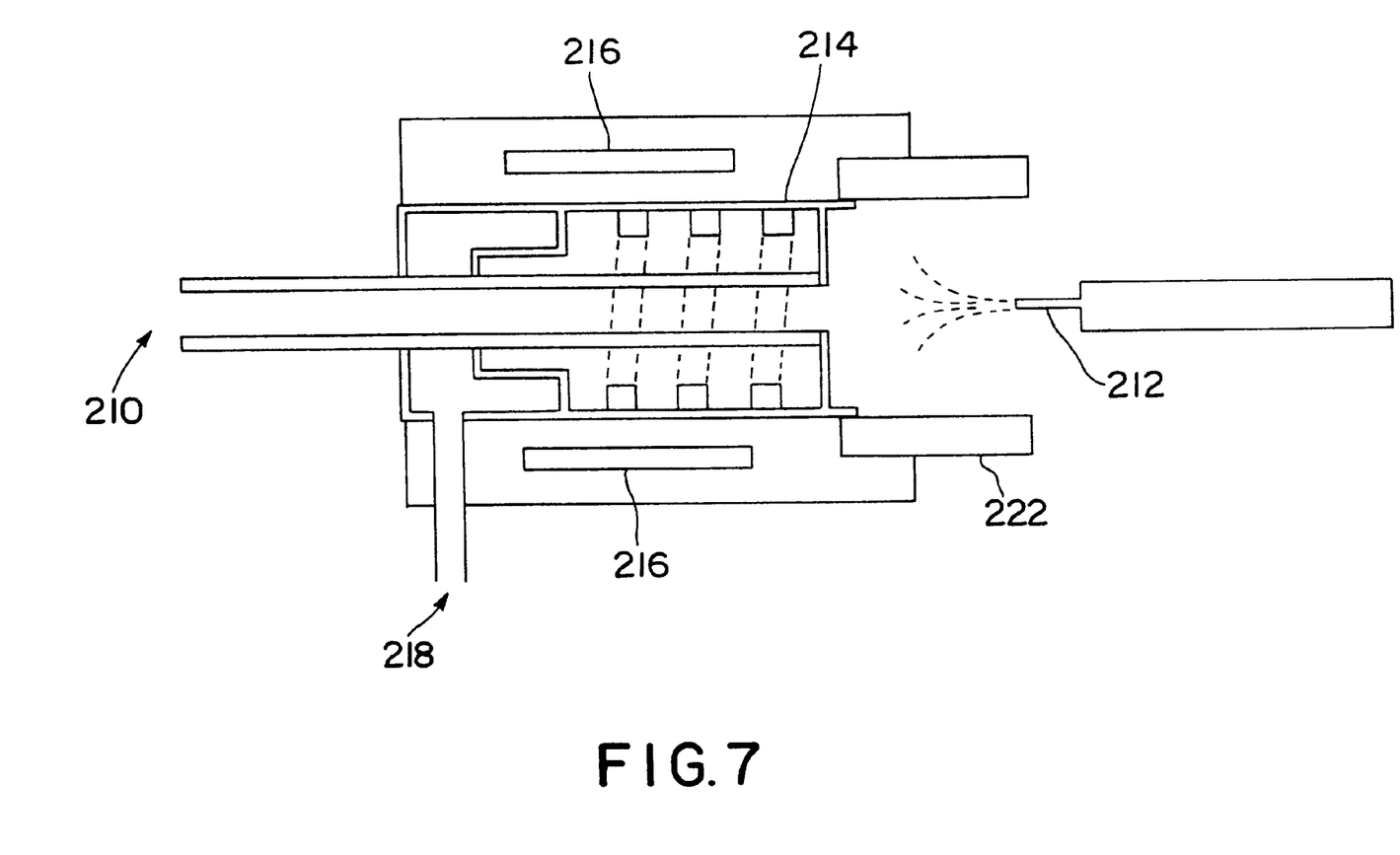

FIG. 7 is a schematic diagram showing another alternative arrangement of the vortex gas flow interface of FIG. 3 and an electrospray needle. In the embodiment of FIG. 7, the axis of electrospray needle 212 is coaxial with the entrance of central capillary 210.

Figure 8:
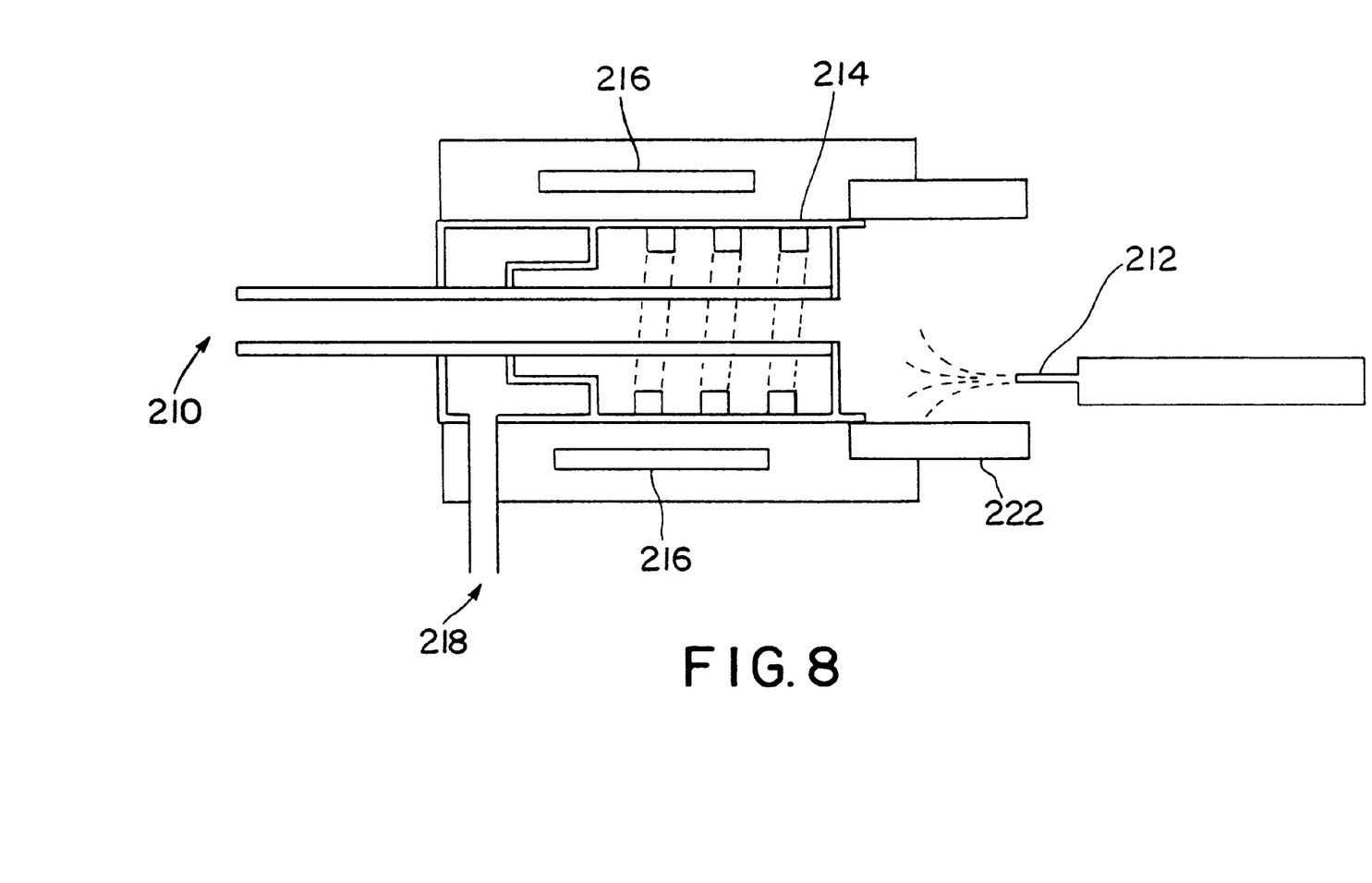

FIG. 8 is a schematic diagram showing still another arrangement of the vortex gas flow interface of FIG. 3 and an electrospray needle. In the embodiment of FIG. 8, the axis of electrospray needle 212 is displaced from the axis of the entrance to central capillary 210, but parallel to it.

Figure 9:
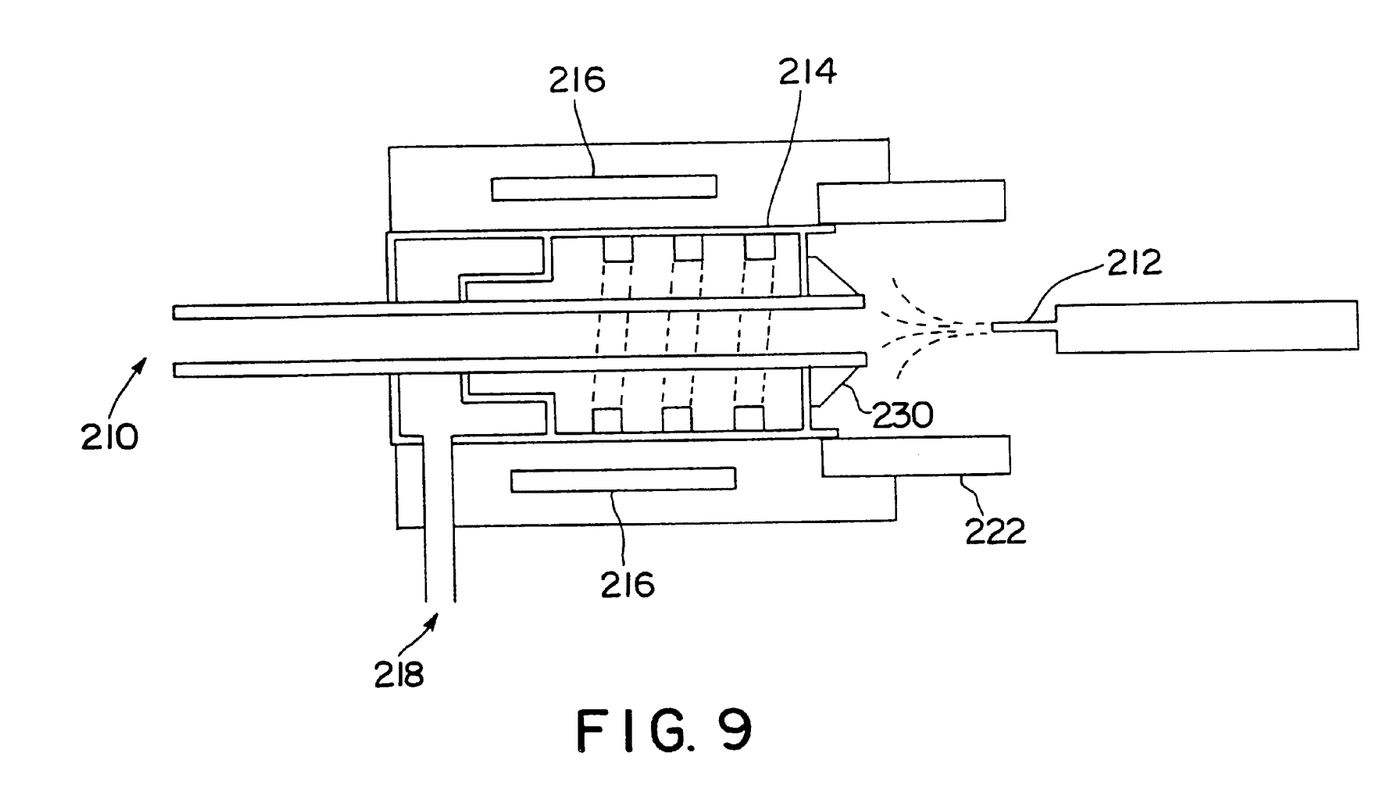

FIG. 9 is a diagram showing a different embodiment of the vortex gas flow interface of the present invention. In the embodiment of FIG. 9, a sampling tip 230 has been added to central capillary tube 210. Sampling tip 230 may be tapered at an angle as shown in the figure. It may also take the form of a thin walled extension of central tube 210 away from the vortex forming structure and further into the vortex flow in drying tube 222, to optimize the pressure region in which the ions are sampled into the central capillary entrance.

Sampling tip 230 is used to locate the entrance of capillary 210 in the optimal region of the vortex formed by the vortex forming channels. There is a stagnant region on the front surface of the vortex forming structure between the exit of the gas channels and the opening into the vacuum chamber (i.e. capillary exit, or aperture). It is possible that large droplets could enter this region and be sucked into the opening to the vacuum chamber. By extending the opening away from the front surface of the vortex forming structure, large droplets are forced to encounter the gas flow and are displaced from the opening.

Figure 10:
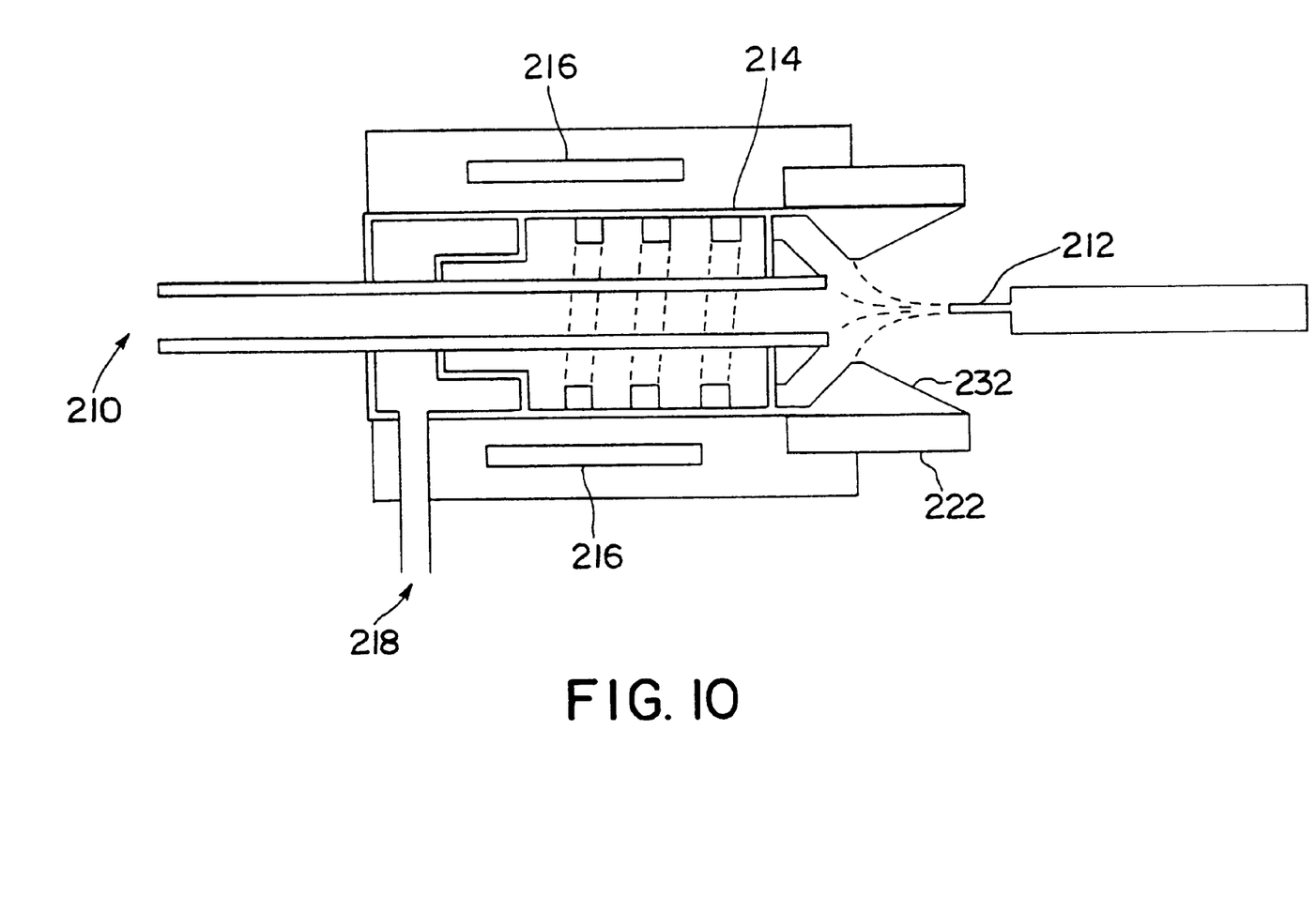

FIG. 10 is a diagram showing yet another embodiment of the vortex gas flow interface of the present invention. In the embodiment of FIG. 10, a flow shaping structure 232 has been added to vortex drying tube 222 so that the angular velocity of the gas is increased in the region in front of the entrance to capillary 210. In combination with the sampling tip of FIG. 9, the flow shaping structure can be used to optimize the ion sampling process into the capillary entrance.

Figure 11:
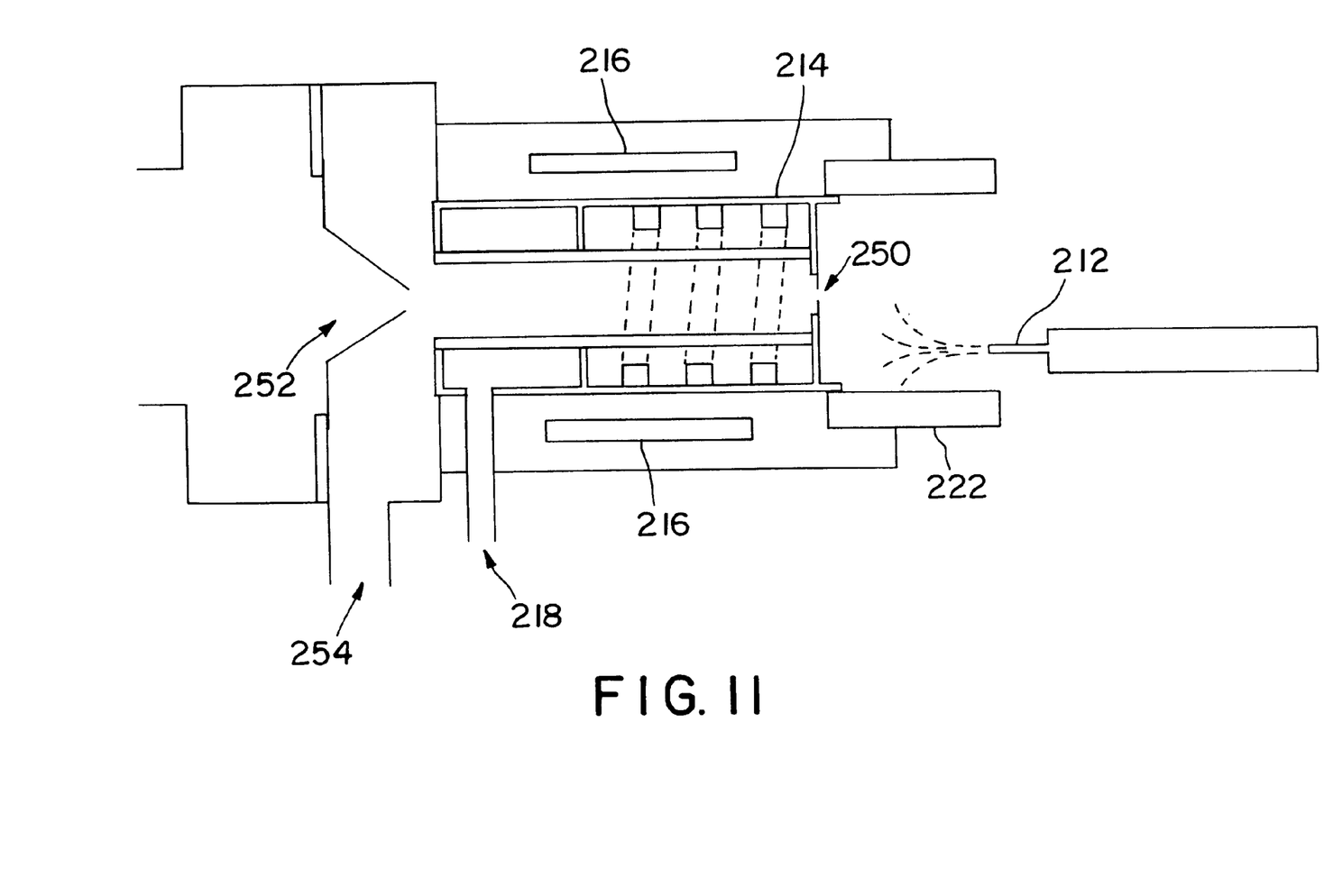
Figure 12:
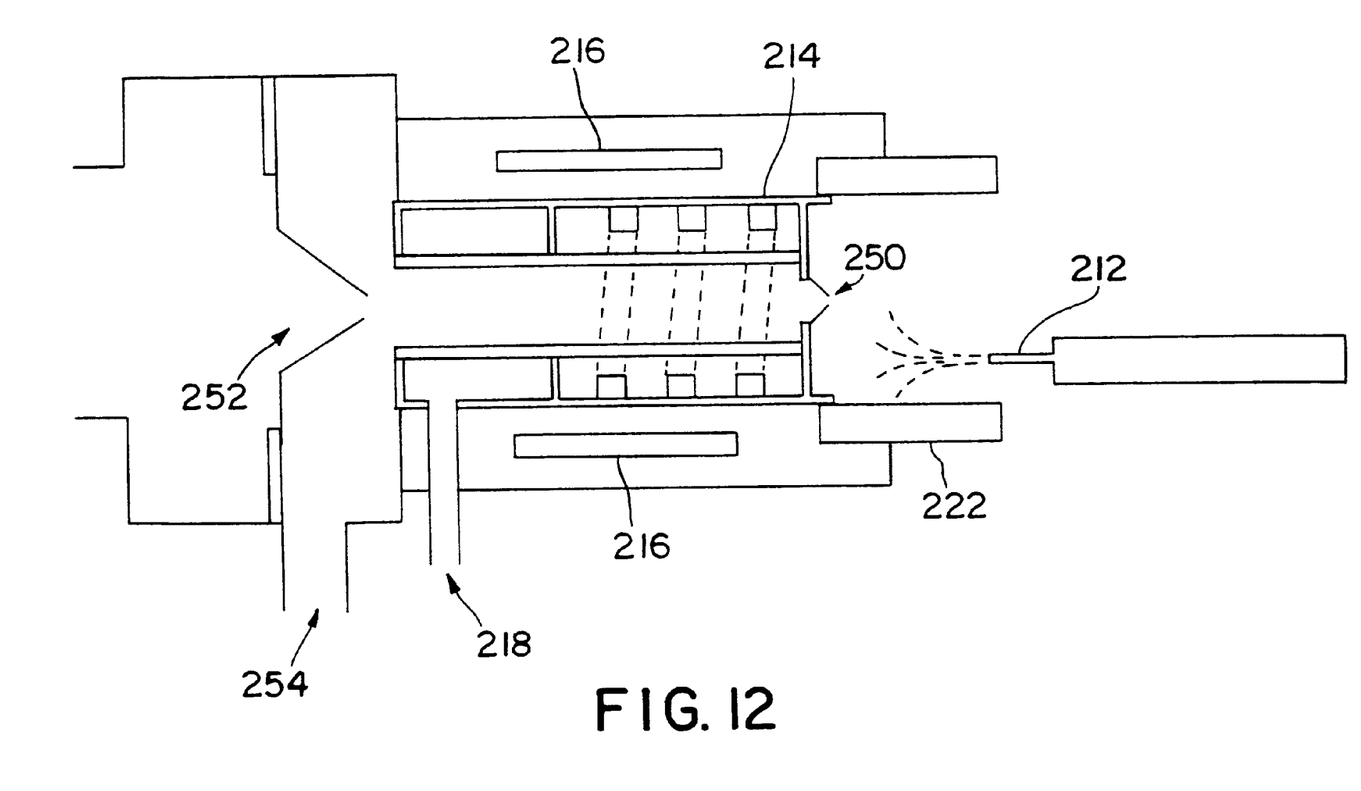

FIGS. 11 and 12 are schematic diagrams showing an embodiment of the present invention which incorporates a sampling orifice 250 and skimmer cone 252. FIG. 11 shows the use of a flat sampling orifice, while FIG. 12 shows the use of a conical sampling orifice to sample the ions from the vortex region into the first stage of the vacuum system. Gas traversing such small orifices, with a large pressure drop across them, undergoes a supersonic expansion. Skimmer cone 252 is often positioned down stream from the orifice and located within the silent zone, where the molecular motion is unidirectional. The gas jet that emerges from the other side of the skimmer, in which the sample ions are entrained, is directed towards the mass analyzer section of the mass spectrometer. Excess gas outside of the silent zone in the region up stream from the skimmer cone is typically removed by a vacuum pump through outlet 254.

The various embodiments of the present invention disclosed herein exemplify different ways of optimizing the performance of the interface. Typically, the parameters to be optimized are: (1) maximize the signal of interest; and (2) minimize the noise due to large charged droplets. The optimum conditions may be different due to the use of different flow rates and liquid compositions.

Alternate embodiments for vortex drying tube 222 include: (1) making it of a conducting material; and (2) making the tube of a resistive material so that as charge accumulates along the surface of the tube from collisions with the charged drops, a potential difference is generated along the length of the tube due to the current flowing to ground. This will produce a potential gradient in a direction that drives the ions toward the central capillary aperture. Yet another embodiment could utilize a grounded needle and bias the vortex structure and the end of the central capillary tube at the appropriate voltage to induce electrospray ionization.

Note that the choice of drying tube material also involves optimizing the signal-to-noise ratio. High liquid flow rate and liquids that are susceptible to forming large droplets (i.e. high aqueous content liquids) may create too much charging of the drying tube surface and require a means of dissipating the charge, by utilizing a resistive or even a conductive surface.

It will be recognized that there are many variations and combinations of the embodiments described herein that are within the spirit of the invention. For example, a variety of mechanical structures can be used to create a vortex gas flow. The vortex forming structure can be made from a plurality of gas delivery tubes that are located on the end of, and tangent to, the drying tube. If the tubes are positioned with a helix angle similar to that of the multi-start threaded structure described herein, the resulting gas flow will form a vortex flow. Similarly, as shown in FIGS. 11 and 12, the central capillary tube could be replaced or augmented by a skimmer cone or orifice in a flat plate.

Novel features of the present invention include: (1) formation of a vortex drying gas flow, symmetrically disposed around and transverse to the axis of a central capillary tube entrance to a mass spectrometer, to impart a centrifugal force to the drops and separate out the large drops formed when using electrospray ionization for high sample liquid flow rates; (2) use of an electrically insulating vortex drying tube to confine charged drops in the radial direction as they move towards the inlet to the mass spectrometer; (3) improvement of the transport of charged sample into a mass spectrometer by enhancing the pressure gradient between the entrance to the mass spectrometer and the surrounding gas containing the electrosprayed drops; and (4) use of a capillary tube, skimmer cone, or orifice that extends into the low pressure region of the vortex flow to optimally sample the desolvated ions.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

What is claimed is:

1. An electrospray interface apparatus comprising:
   transport means for coupling the spray from an electrospray needle to a low pressure region, said transport means having an entrance port for receiving said spray;
   means for applying a centrifugal force to the spray, comprising a source of a heated gas; and a structure for forming a vortex gas flow from the heated gas in a direction substantially transverse to the entrance to the mass analyzer; and
   an output port for providing the output of the interface apparatus to the entrance of a mass analyzer.

2. The apparatus of claim 1, wherein the structure for forming a vortex flow further comprises:
   a plurality of channels arranged symmetrically around the entrance to the mass analyzer and connected to the source of heated gas.

3. The apparatus of claim 1, wherein the vortex gas flow encounters the spray from the electrospray needle in a region bounded by an insulating material.

4. The apparatus of claim 3, wherein the insulating material is quartz.

5. An electrospray apparatus, comprising:
   an electrospray needle for performing electrospray ionization of a liquid sample matrix; and
   an interface arranged between an output of the electrospray needle and the entrance to a mass analyzer, the interface further comprising
   transport means for coupling the output of the electrospray needle to a lower pressure region, said transport means having an entrance port for receiving said output;
   means for applying a centrifugal force to the electrospray needle output comprising a source of a heated gas and a structure for forming a vortex flow from the heated gas in a direction substantially transverse to the entrance to the mass analyzer; and
   an output port for providing the output of the interface to the entrance of the mass analyzer.

6. The apparatus of claim 5, wherein the structure for forming a vortex flow further comprises:
   a plurality of channels arranged symmetrically around the entrance to the mass analyzer and connected to the source of heated gas.

7. The apparatus of claim 5, wherein the output of the electrospray needle is directed at an angle to the entrance to the mass analyzer.

8. The apparatus of claim 5, wherein the output of the electrospray needle is directed parallel to the entrance to the mass analyzer.

9. The apparatus of claim 5, wherein the vortex gas flow encounters the output of the electrospray needle in a region bounded by an insulating material.

10. The apparatus of claim 9, wherein the insulating material is quartz.

11. A method of reducing noise generated by the introduction of large drops into the sample acceptance region of the mass analyzer of a mass spectrometer system, comprising:

provided a bounded region which substantially surrounds the large drops; and applying a centrifugal force to the drops forming a vortex flow of gas in a direction substantially transverse to a direction of flow of the drops, thereby causing the drops to be driven into the bounding surfaces of the region.

12. The method of claim 11, wherein the large drops are formed by electrospray ionization.

* * * * *